US005840689A

United States Patent [19]

Daniloff

[11] Patent Number: 5,840,689
[45] Date of Patent: Nov. 24, 1998

[54] METHOD FOR STIMULATING THE REGROWTH OF NEURONS

[75] Inventor: Joanne K. Daniloff, Baton Rouge, La.

[73] Assignee: Board of Supervisors of Louisiana State University and Agricultural and Mechanical College, Baton Rouge, La.

[21] Appl. No.: 458,555

[22] Filed: Jun. 2, 1995

Related U.S. Application Data

[63] Continuation of Ser. No. 146,734, Oct. 29, 1993, abandoned.
[51] Int. Cl.$^6$ ............................ A61K 38/17; A61K 38/39
[52] U.S. Cl. .................................................. 514/12; 514/2
[58] Field of Search .......................... 514/2, 12; 435/69.1

[56] References Cited

U.S. PATENT DOCUMENTS 4,955,892  9/1990  Daniloff .................................. 606/152

OTHER PUBLICATIONS

Dodd et al., Science 242 692–699 (1988).
Doherty et al Nature 343 464–466 (1990).
Cunningham et al., Science 236 799–806 (1987).
Caroni et al, J. Cell Biology, v106, 1988, pp. 1281–1288.
J. Dodd et al., "Axon Guidance and the Patterning of Neuronal Projections in Vertebrates," Science, vol. 242, pp. 692–699 (1988).
P. Doherty et al., "A Threshold Effect of the Major Isoforms of NCAM on Neurite Outgrowth," Nature, vol. 343, pp. 464–466 (1990).
B. Cunningham et al., "Neural Cell Adhesion Molecule: Structure, Immunoglobulin–Like domains, Cell surface Modulations, and Alternative RNA Splicing," Science, vol. 236, pp. 799–806 (1987).
P. Caroni et al. "Two Membrane Protein Fractions from Rat Central Myelin with Inhibitory Properties for Nuerite Growth and Fibroblast Spreading," J. Cell Biol., vol. 106, pp. 1281–1288 (1988).
K. Gibson et al., "Peripheral Nerve Repair," Compend. Contin. Educ. Pract. Vet., vol. 11, pp. 938–945 (1989).

J. Daniloff et al., "Altered Expression of Neuronal Cell Adhesion Molecules Induced by Nerve Injury and Repair," J. Cell Bio., vol. 103, pp. 929–945 (1986).
M. Walker, "Acute Spinal Cord Injury," New Eng. J. Med., vol. 324, pp. 1885–1887 (1991).
K. Gibson et al., "Comparison of Sciatic Nerve Regeneration through Silicone Tubes and Nerve Allografts," Microsurg., vol. 10, pp. 126–129 (1989).
K. Gibson et al., "Comparison of Nerve Regeneration through Different Types of Neural Prostheses," Microsurg., vol. 12, pp. 80–85 (1991).
J. Daniloff, "A Novel Assay for in vivo Study of Schwann Cells," Experimental Neurology, vol. 114, pp. 140–143 (1991).
T. Frei et al., "Different Extracellular Domains of the Neural Cell Adhesion Molecule (N–CAM) Are Involved in Different Functions," J. Cell Biol., vol. 118, pp. 177–194 (1992).
L. Remsen et al., "Antibodies to the Neural Cell Adhesion Molecule Disrupt Functional Recovery in Injured Nerves," Exp. Neurol., vol. 110, pp. 268–273 (1990).
J. Daniloff et al., "Differential Distribution of Cell Adhesion Molecules During Histogenesis of the Chick Nervous System," J. Neuroscience, vol. 6, pp. 739–758 (1986).

*Primary Examiner*—Lora M. Green
*Assistant Examiner*—Stephen Gucker
*Attorney, Agent, or Firm*—John H. Runnels

[57] ABSTRACT

A method is disclosed for enhancing the repair of injured neurons, where the site of injury is either within nerves of the peripheral nervous system, or within neural pathways of the central nervous system. The repair of a neuron may be enhanced by the application of the neural cell adhesion molecule (N-CAM) or a subunit of N-CAM to the site of the injury, particularly in the absence of any exogenous device such as a tube surrounding the immediate site of the injury. The method (1) maximizes recovery in severe nerve injuries, and (2) provides the first successful treatment ever reported for spinal cord injuries. Most physicians and veterinarians will be able to use the novel method of treatment without substantial additional training, as special surgical skills are not needed.

18 Claims, 6 Drawing Sheets

METHOD FOR STIMULATING THE REGROWTH OF NEURONS

This is a continuation of application Ser. No. 08/146,734, filed Oct. 29, 1993, now abandoned.

This invention pertains to methods for stimulating the regrowth of injured neurons, for example, stimulating the regrowth of injured nerves in the peripheral nervous system or the regrowth of an injured spinal cord.

The peripheral nervous system (PNS) comprises highly organized groups of axon fibers or nerves external to the brain and spinal cord, such as the nerves in the limbs. In response to nerve damage, the peripheral nervous system often attempts to repair itself. However, the return of lost functions is usually incomplete.

By contrast, damage to the central nervous system (CNS), comprising the brain and spinal cord, is generally more serious, causing permanent losses having broad ramifications that can include death.

A number of conditions are known to affect both growth and spontaneous regeneration in nerves, but the underlying mechanisms are not well understood. K. Gibson et al., "Peripheral Nerve Repair," *Compend. Contin. Educ. Pract. Vet.*, vol. 11, pp. 938–945 (1989); and J. Daniloff et al., "Altered Expression of Neuronal Cell Adhesion Molecules Induced by Nerve Injury and Repair," *J. Cell Bio.*, vol. 103, pp. 929–945 (1986). These conditions include the location of injury, the type of injury, the severity of injury, and the age and general health of the patient. For example, a poor case for spontaneous recovery would be an elderly patient hospitalized with a transected nerve close to the spinal cord. By contrast, spontaneous recovery would normally be expected in a young person in good health with a severed nerve in a finger.

It has been reported that minor prior recoveries somehow prime the nerve for greater recovery in secondary lesions, for example, recovery from an earlier compression injury. See generally K. Gibson et al. (1989) and J. Daniloff et al. (1986), cited above.

There are no previous reports of an effective treatment for injuries to neurons of the central nervous system, the brain and spinal cord. See M. Walker, "Acute Spinal Cord Injury," *NewEng. J. Med.*, vol. 324, pp. 1885–1887 (1991).

The lack of effective treatments for nervous system injuries may be due to an insufficient understanding both of the formation of the nervous system and of its responses to injuries. Several attempts have been made to electrically stimulate injured nerves to try to cause regrowth; recovery was highly variable and inadequate. See B. Sisken et al., "Pulsed Electromagnetic Fields Stimulate Nerve Regeneration in vitro and in vivo," Restorative Neurology and Neuroscience, vol. 1, pp. 303–309 (1990); see generally J. Daniloff et al., "The Molecular Bases of Nerve Regeneration," in S. Malhotra (ed.), *Advances in Neural Science*, vol. 2 (in press, 1993). The method that is currently used most often to close gaps in severed nerves uses grafts of the patient's own sensory nerves, typically taken from the ankle; a minimal degree of recovery and permanent analgesia of the donor foot are the usual results.

A prior technique for repairing nerve injuries involved placing a tube of an inert material between the severed ends of a nerve to close the gap. The tube enhances recovery of the nerve, but the tube must be removed within approximately thirty days. The tube serves as a conduit for regrowing nerve fibers, and traps trophic factors within the lesion during initial stages of regeneration. However, the tube eventually constricts the regenerating fiber by limiting outgrowth to the dimension of the tube. Ultimately, the presence of the tube incites the formation of scar tissue around the regenerated nerve; by contrast, such scar tissue is not seen following a nerve graft. The scar swells to constrict (and potentially injure) the regenerated fiber. See K. Gibson et al., "Comparison of Sciatic Nerve Regeneration through Silicone Tubes and Nerve Allografts," Microsurg., vol. 10, pp. 126–129 (1989); and K. Gibson et al., "Comparison of Nerve Regeneration through Different Types of Neural Prostheses," *Microsurg.*, vol. 12, pp. 80–85 (1991).

L. Remsen et al., "Antibodies to the Neural Cell Adhesion Molecule Disrupt Functional Recovery in Injured Nerves," Exp. *Neurol.*, vol. 110, pp. 268–273 (1990) reported a significant slowing of spontaneous recovery in severed sciatic nerves when N-CAM function was blocked immunologically; these results suggested that N-CAM may contribute to spontaneous nerve regeneration.

U.S. Pat. No. 4,955,892, the entire disclosure of which is incorporated by reference, discloses a process for repairing a severed nerve in the peripheral nervous system, in which the severed nerve ends were placed in a prosthetic device, such as a tube, that contained a quantity of N-CAM. In a preferred embodiment, the N-CAM was embedded in a semi-solid collagen matrix. There was no suggestion to use N-CAM in the absence of a prosthetic device such as a tube, nor was there any suggestion of a method to repair neurons in the central nervous system.

Schwann cells, the cells that form the sheath enveloping a nerve fiber, can produce N-CAM under conditions of embryonic development. Transplantation of Schwann cells into severed sciatic nerves promotes regeneration that exceeds that achieved with nerve grafts. See J. Daniloff et al., "A Novel Assay for in vivo Study of Schwann Cells," *Experimental Neurology*, vol. 114, pp. 140–143 (1991). The spinal cord and other CNS regions lack Schwann cells.

Although there have been some prior treatments for injured nerves in the peripheral nervous system, there have been no prior successful treatments for spinal cord injuries.

Damage to the CNS has been observed to induce axonal sprouting and elongation for a few millimeters in rodents. But the spinal cord will not repair itself to any significant degree, at least in part because scars form that eventually block the slow and minor regrowth of CNS fibers.

Because an injured spinal cord has very limited ability to recover spontaneously, and because the consequences of spinal cord injuries can be so serious, there is a particular need for an effective treatment of spinal cord injuries. Paralytic spinal cord injuries in the United States alone occur at the rate of about 10,000 per year. Fewer than 10% of the injured die, leaving approximately 720 Americans per million population permanently disabled as the result of spinal cord injuries. Most of the injured are young people in the most productive stage of life. No effective treatment for spinal cord injuries currently exists. M. Walker, "Acute Spinal Cord Injury," *NewEng. J.Med.*, vol. 324, pp. 1885–1887 (1991).

Previous treatments for patients with spinal cord injuries have not been successful in inducing recovery of function. Immobilization of the injured area improves patient survival rates, but results in no measurable recovery of function. Electrical stimulation of the spinal cord after injury produces no more than an insignificant recovery of function. Experimental implantation of nerves in the area of the injury supports some fiber regrowth, but any recovery of function is insignificant. S. David et al., "Axonal Elongation into Peripheral Nervous System 'Bridges' after Central Nervous System Injury in Adult Rats," *Science*, vol. 214, pp. 931–933

(1981). Application of nerve growth factor in the area of the injury may prevent cell death, but produces no significant recovery of function. D. Otto et al., "Pharmacological Effects of Nerve Growth Factor and Fibroblast Growth Factor Applied to Transected Sciatic Nerve on Neuron Cell Death in Adult Dorsal Root Ganglia," *Neurosci. Lett.*, vol. 83, pp. 156–160 (1987). Intravenous administration of gangliosides has been reported to yield some improvement in some patients, but results have not been consistent. Injection of the steroid sodium methyl-prednisolone in the spinal cord at very high dose levels (30 mg/kg) and physical therapy have both been reported to yield minor, albeit inconsistent, improvement in some patients with compression or contusion injuries. No human clinical trials for any treatment of spinal cord damage are believed to be underway at the time of the filing date of this application.

Neural cell adhesion and bonding are important in the formation of the nervous system. The neural cell adhesion molecule, or N-CAM, is a sialoglycoprotein that supports the earliest stages of nervous system development. Normally, the E-form of N-CAM is not expressed after development stops, and is only found in minute levels in those rare areas of the adult CNS that have some degree of plasticity (the olfactory bulb, dorsal root ganglia, and cerebellum). The adult A-form of N-CAM is retained in all neural tissues throughout life. See J. Daniloff et al., "Differential Distribution of Cell Adhesion Molecules During Histogenesis of the Chick Nervous System," *J. Neuroscience*, vol. 6, pp. 739–758 (1986); J. Daniloff et al., "Altered Expression of Neuronal Cell Adhesion Molecules Induced by Nerve Injury and Repair," J. Cell Bio., vol. 103, pp. 929–945 (1986); and G. Edelman, "Cell Adhesion Molecules," *Science*, vol. 219:450–457 (1983). N-CAM is found primarily in neural cell membranes. The N-CAM protein backbone contains three polypeptide chains having molecular weights of 120 kD, 140 kD, and 170–200 kD as measured on SDS-PAGE gels; the molecular weight of the largest of the three polypeptide chains varies with the content of attached sialic acid. See G. Edelman, "Cell Adhesion Molecules," *Science*, vol. 219:450–457 (1983).

During nervous system development, the embryonic (E) form of N-CAM, which is rich in sialic acid, predominates. As development proceeds, N-CAM (E) is replaced by the adult N-CAM (A) form, which has significantly less sialic acid. This conversion results exclusively from the alternate splicing of one gene. The A-form stabilizes the rate and strength of binding, while the E-form promotes temporary and weak binding. See G. Edelman, "Cell Adhesion Molecules," *Science*, vol. 219:450–457 (1983). Each N-CAM component may make distinct contributions to the development of the brain. The 140 kD polypeptide has been reported to be the most active stimulant of neuron fiber outgrowth in embryos. T. Frei et al., "Different Extracellular Domains of the Neural Cell Adhesion Molecule (N-CAM) Are Involved in Different Functions," *J. Cell Biol.*, vol. 118, pp. 177–194 (1992).

A novel method has been discovered to enhance the repair of injured neurons, either in nerves of the peripheral nervous system or in neural pathways of the central nervous system. The repair of an injured neuron or neurons may be enhanced by the application of N-CAM or a subunit of N-CAM to the site of the injury, preferably in the absence of any exogenous device such as a tube surrounding the immediate site of the neural injury. The novel method (1) maximizes recovery in severe nerve injuries, and (2) provides the first successful treatment for recovery of function following a severe spinal cord injury. The successful treatment of spinal cord injuries is particularly surprising, as there has been no prior teaching that an injured spinal cord possesses any plasticity Most physicians and veterinarians will be able to use the novel method of treatment without substantial additional training, as special surgical skills are not needed.

BRIEF DESCRIPTION OF THE PHOTOGRAPHS

FIG. 2 is a photomicrograph of a transected sciatic nerve with no treatment.

FIG. 3 is a photomicrograph of a sectioned sciatic nerve treated with an inert gel in a tube.

FIG. 4 is a photomicrograph of a sectioned sciatic nerve treated with N-CAM in a tube.

FIG. 5 is a photomicrograph of a sectioned sciatic nerve treated with N-CAM, without a tube or other prosthesis.

Materials and Methods

Figure 1:
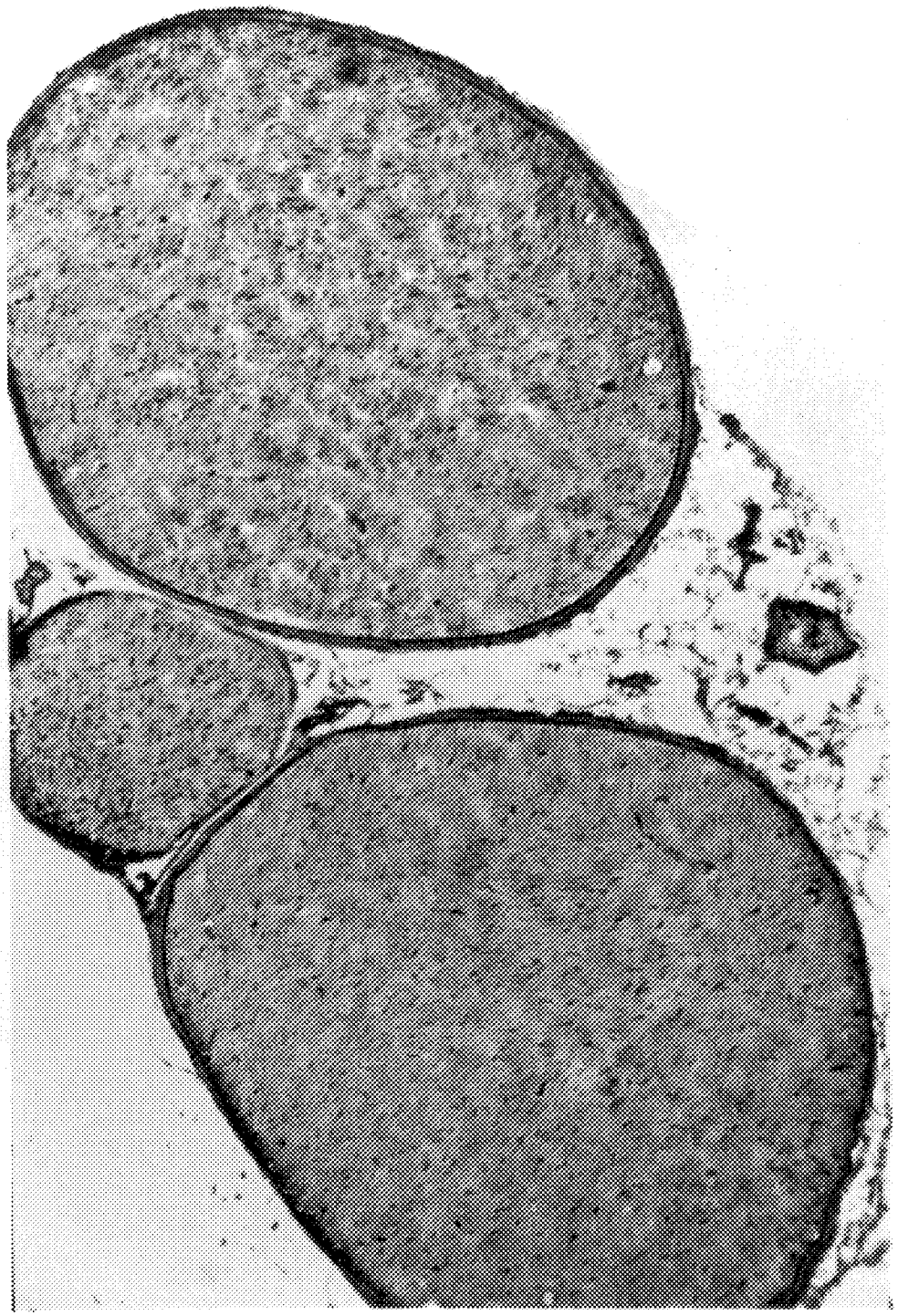
FIG. 1 is a photomicrograph of a cross-section of uninjured sciatic nerve.

1. Isolation and Immunologic Purification of N-CAM Protein.

Mouse hybridoma cells secreting monoclonal rat N-CAM antibodies (IgM) were produced by the method of L. Remsen et al., "Antibodies to the Neural Cell Adhesion Molecule Disrupt Functional Recovery in Injured Nerves," 1 *Exp. Neurol.*, vol. 110, pp. 268–273 (1990), whose entire disclosure is incorporated by reference. Briefly, N-CAM-containing membrane components were isolated from fetal rat brain tissues via sucrose gradient ultracentrifugation, and then injected into mice primed with *Bordetellapertussis* (Wako Chemicals, Dallas, Tex.). Subcutaneous booster immunizations were administered containing live, dissociated, fetal rat brain cells. Antibodies were coupled to cyanogen bromide-activated sepharose CL-4B beads (Pharmacia, Piscataway, N.J.) for affinity purification, and then packed into chromatography columns. N-CAM was extracted from homogenized fetal brains and purified by column elution. 2. Surgical Treatment of Nerves. In fifteen young adult rats, 10 mm of sciatic nerve (about ⅓ the length of the femur) was removed to induce a severe injury. One of three treatments was applied: (1) N-CAM in an inert gel administered in a tube, (2) an inert gel administered in a tube, or (3) N-CAM in an inert gel deposited without any tube. Recovery was assayed 30 days post-surgery, followed by euthanasia. Sterile, inert, silastic tubes were used for nerve entubulization (inner diameter 0.78 mm, outer diameter 1.25 mm; Dow Corning, Midland, Mich.). Experimental tubes contained N-CAM admixed in gel (2.5 $\mu$g N-CAM/5 $\mu$l gel), while control animals received tubes containing agarose gel only. Agarose, an inert derivative of seaweed (1.5%/PBS; Sigma Corp., St. Louis), was the carrier for N-CAM in both the direct application and in the entubulization (2.5 $\mu$g/5$\mu$l gel). In the third treatment, the N-CAM/gel was deposited directly on the lesion without entubulization. 3. Electrodiagnostic Assessment of Recovery. Motor unit potentials were evoked to compare normal and experimental functions. Normal function was recorded in all animals prior to surgery to obtain baseline function. Peak amplitudes of summated rat muscle motor unit potentials were recorded with a 4-channel TECA recording system (Pleasantville, N.Y.). The degree of recovery was assessed in treated sciatic nerves. Nerves were stimulated with Teflon-coated, atraumatic straight needles at the level of the greater trochanter of the femur to deliver single rectangular pulses of supramaximal strength (60 V, 100 $\mu$s duration). In each stimulating cathode the terminal 5 mm of coating was removed, and was then positioned approximately 0.5 cm distal to the anode. Bipolar recording electrodes were centered in the muscle belly, with a ground electrode placed subcutaneously between stimulating and recording systems.
4. Surgical Treatment of Spinal Cords. Spinal cords of eighteen young adult, Sprague-Dawley rats (6 months old) were exposed via laminectomy and hemisected at thoracic level 12 to cause paralysis of one hindlimb. Nine of the rats were treated immediately with an intrathecal application of N-CAM in agarose gel at a concentration of 10 $\mu$g/10 $\mu$l. The remaining nine animals received only agarose gel as a control. Recovery was assessed 60 days post-surgery, followed by euthanasia. The speed of electrical transmission (conduction velocity) in motor tracts was tested in treated spinal cords to measure the extent of recovery.

An additional measure of recovery was the observation of the ability of the afflicted limb to participate in normal walking movements, as measured by a "walking track index." The "walking track index" was a numerical measurement of walking ability derived from analyses of paw prints on paper strip charts traversed by the rats. Non-toxic black ink was placed on the bottom of each hind paw, and non-toxic red ink on the top of each hind paw. The record of black and red marks left on a chart indicated the ability of the rat to use the affected limb. At one extreme, black marks with individual toe prints evidenced normal function; and at the other extreme, amorphous red smears evidenced total loss of function. Intermediate recovery of function was evidenced by the color and shape of the marks left on the paper.

The walking track index was based on mean, normalized scoring in accordance with the following scale, in which 7 was considered normal and 0 nonfunctional:

| Score | Affected Limb Locomotor Function | Footprints from Affected Limb |
|---|---|---|
| 0 | No voluntary movement; limb held in loosely extended position while dragged | Uninterrupted red line |
| 1 | No weight bearing, with a tendency to carry the leg flexed against the trunk | Absence of print marks, or an occasional red mark |
| 2 | Partial weight bearing while walking on dorsum of foot | Red print at the point of weight bearing, with red drag markings behind, in front, or both |
| 3 | Increased weight bearing while walking on dorsum of foot; no digital extensor muscle function | Clearly demarcated red prints; no dragging |
| 4 | Partial placement of foot, usually associated with severe lateral limb rotation, absence of toe spread, and incomplete weight bearing | Black print with red drag markings; associated with variable degree of lateral limb rotation, intermedial toe spread not more than 4 mm, and weight bearing to the extent that the print only consists of digital pads I to IV (i.e., no central foot pad) |
| 5 | Placement of the foot without dragging; lateral limb rotation is still present; toe spread can be seen to various degrees | Complete plantar (black) print with no red marks; intermedial toe spread greater than 4 mm |
| 6 | Placement of foot almost normal | Black print that includes the foot pad with almost normal limb rotation and distinct toe spreading |
| 7 | Placement of foot completely normal with no deficits (i.e., as before an injury) | Completely black prints; normal toe spread and placement |

Results 1. Physiologic Recovery in Sciatic Nerves. In the group treated with N-CAM alone, recovery averaged 54% of normal values. The group treated with N-CAM in tubes recovered 28%. The group average for control recovery was 7%, with only one control subject responding. The N-CAM Treatment recovery was significantly greater than that of the gel Control group ($F=11.5^*, p<0.05$).

Percent Recovery versus Normal Function for Sciatic Nerve Injury (30 day survival)

| A. N-CAM Entubulization | B. N-CAM Application (No Entubulization) | C. Control (Gel) |
|---|---|---|
| (n = 5) | (n = 5) | (n = 5) |
| Mean (S.D.) 28 (20) | 54 (29) | 7 (10) |

$F=11.5^*(p<0.05)$
A vs B, $t=0.1$(n.s.)
A vs C, $t=0.9$(n.s.)
B vs C*, $t=3.1(p<0.05)$

Figure 2:
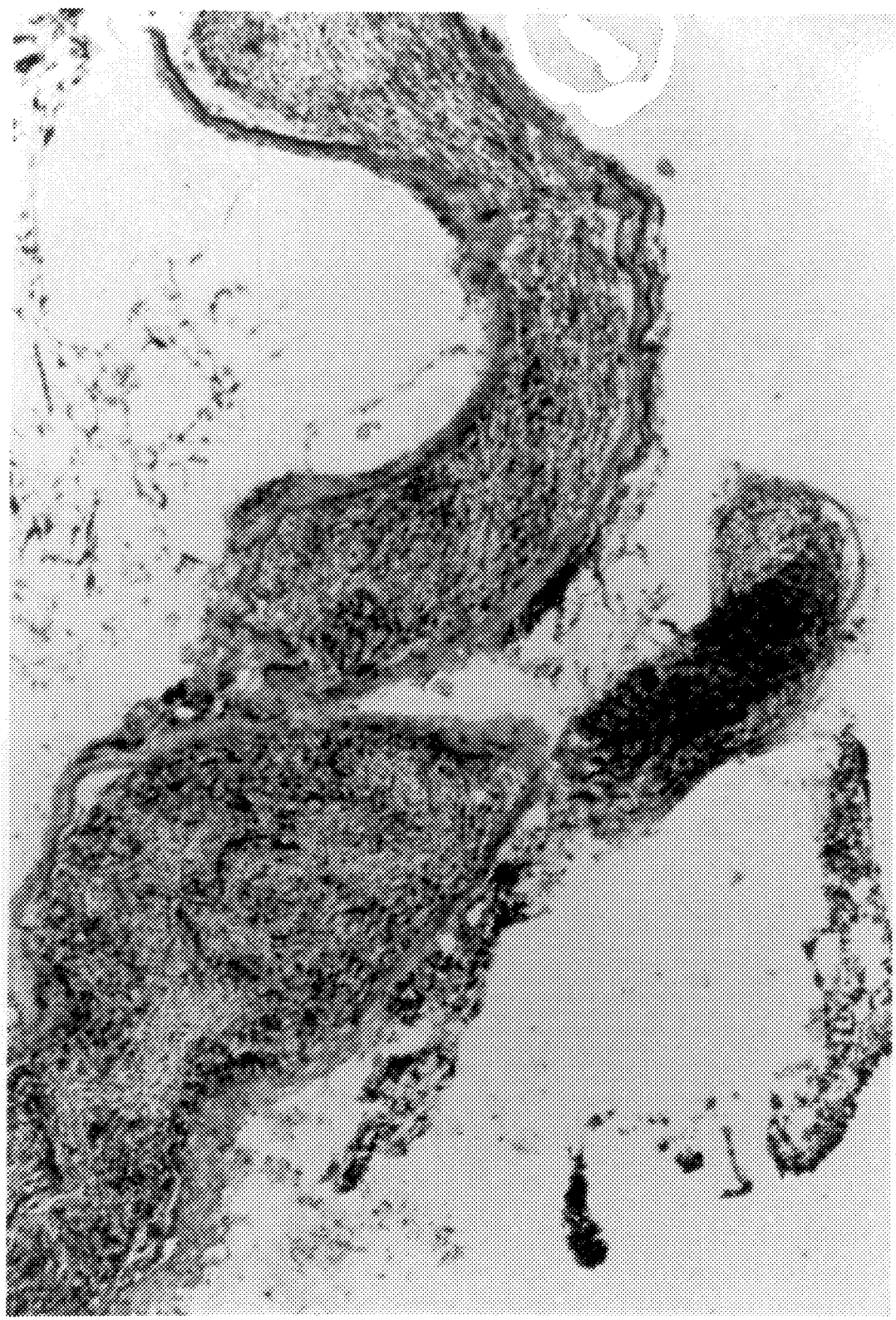
FIGS. 2–5 depict cross-sections of transected sciatic nerves 10 mm distal to the site of injury, 30 days following various treatments, taken from the same site as that depicted in FIG. 1.

The results of morphological studies are illustrated in FIGS. 1–5. FIG. 1 is a photomicrograph of a section of uninjured sciatic nerve. FIG. 2 is a photomicrograph of a section of injured sciatic nerve 30 days after injury, with no treatment. The contrast between FIGS. 1 and 2 is apparent even to the layperson. Little regrowth occurred in the injured, untreated nerve.

Figure 3:
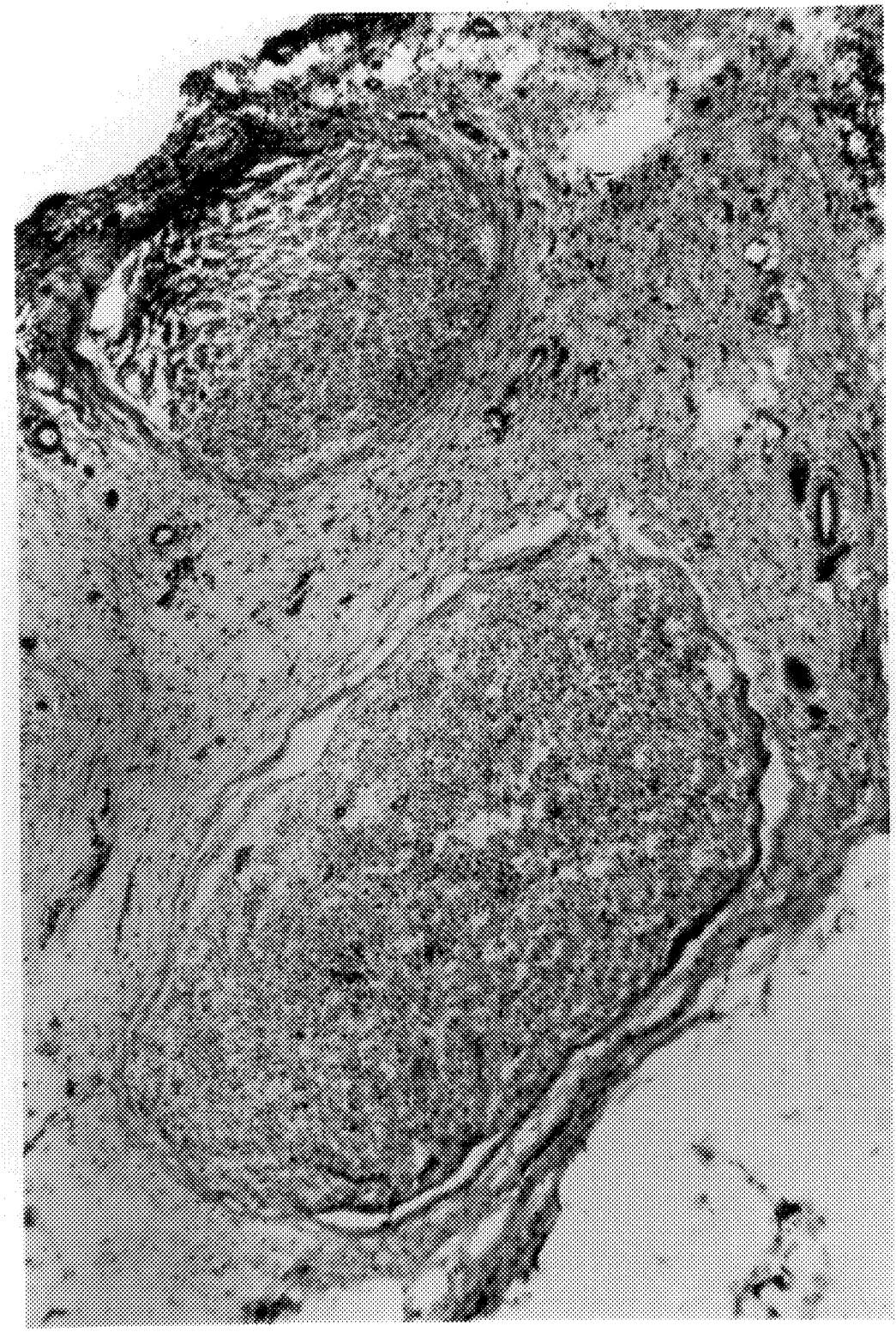

FIG. 3 is a photomicrograph of a section of injured sciatic nerve 30 days after injury, treated with an inert gel in a tube. Compared to the untreated nerve, significant regrowth occurred. However, a substantial amount of scar tissue had grown around the nerve, which would tend to constrict it.

Figure 4:
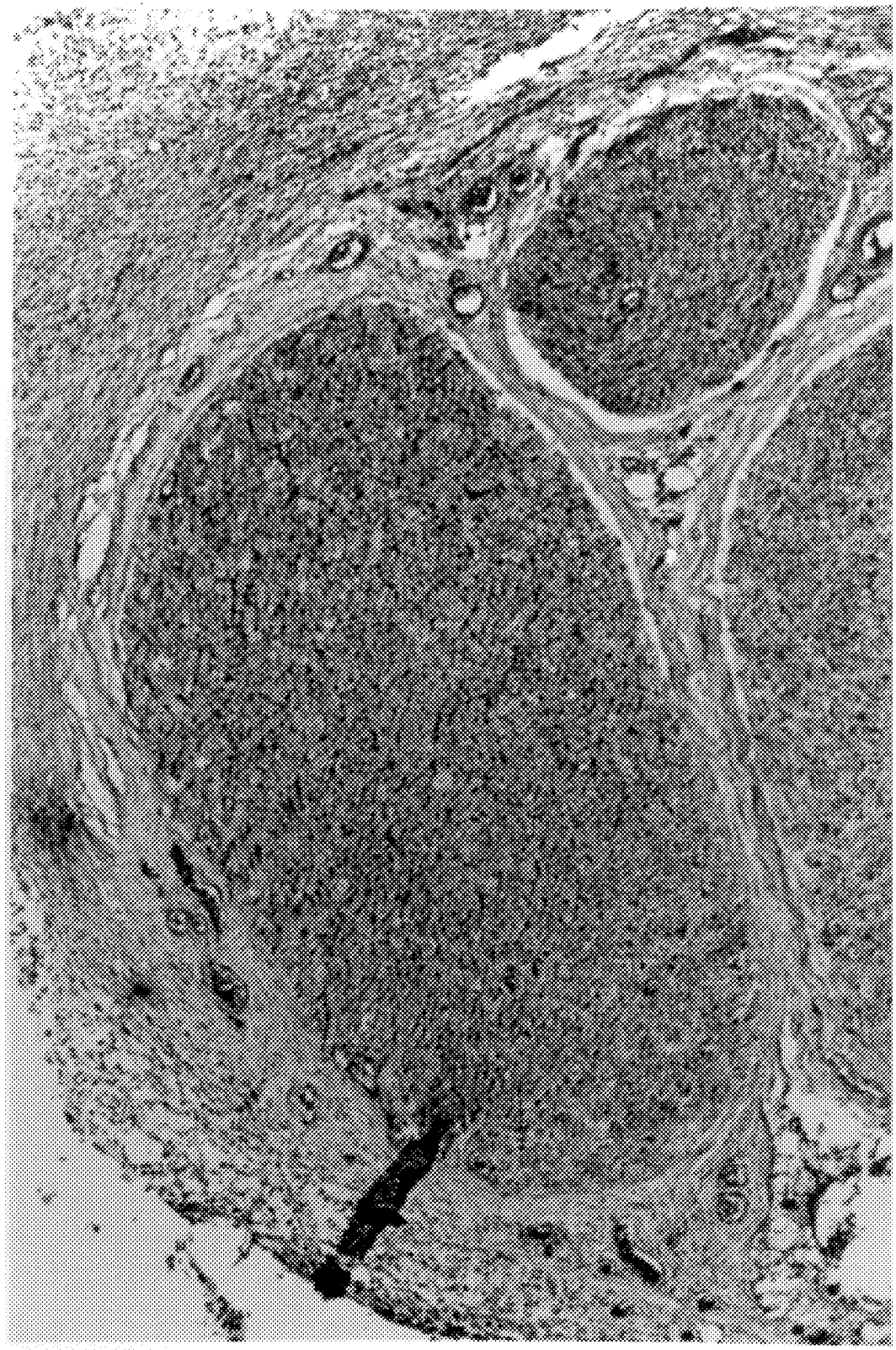

FIG. 4 is a photomicrograph of a section of injured sciatic nerve 30 days after injury, treated with N-CAM in a tube. Compared to the tube without N-CAM, a greater degree of regrowth occurred. However, there was still a substantial amount of scar tissue surrounding the regrown nerve.

Figure 5:

FIG. 5 is a photomicrograph of a section of injured sciatic nerve 30 days after injury, treated with N-CAM without a tube or other prosthesis. Note that the regrown nerve had an appearance very similar to that of the control, uninjured (normal) nerve of FIG. 1. Unlike nerves regrown in a tube, with or without N-CAM (FIGS. 3 and 4), almost no scar tissue was present. 2. Physiologic Recovery in Spinal Cords. After the spinal cord hemisection, in both control and experimental animals the rear limb on the side of the hemisection was initially paralyzed. Recovery of function was monitored by physiologic measurements of electrical conduction velocity, analyses of paw prints during walking, and morphological analyses.

In the control subjects, 27% of normal physiologic (conduction velocity) function, and 28% of normal walking function were recorded 60 days post-surgery. These levels were equated with spontaneous recovery rates, because only one side of the spinal cord was injured.

Percent Recovery of Conduction Velocity versus Normal Function for Spinal Cord Injury (60 day survival)

| A. Experimental: N-CAM Application (n = 9) | | B. Control: Gel (n = 9) |
|---|---|---|
| Mean (S.D.) | 66 (19) | 27 (16) |

A vs B, t=2.98*(p<0.03)

Percent Recovery of Walking Track Index versus Normal Function for Spinal Cord Injury (60 day survival)

| A. Experimental: N-CAM Application (n = 9) | | B. Control: Gel (n = 9) |
|---|---|---|
| Mean (S.D.) | 65 (17) | 28 (22) |

A vs B, t=1.4(n.s.)

Unlike the control animals, the N-CAM-treated animals demonstrated substantial recovery in their use of the paralyzed limb and toes in activities such as walking. The N-CAM treatment significantly enhanced recovery to more than twice that of the control levels: 66% of normal function as measured by conduction velocity, and 65% as measured by the walking track index. (It was noted that the numerical agreement between the conduction velocity measurements and the walking track index measurements was surprisingly close; reanalysis of the underlying data was therefore performed to re-confirm that these numbers were correctly calculated.)

Figure 6:
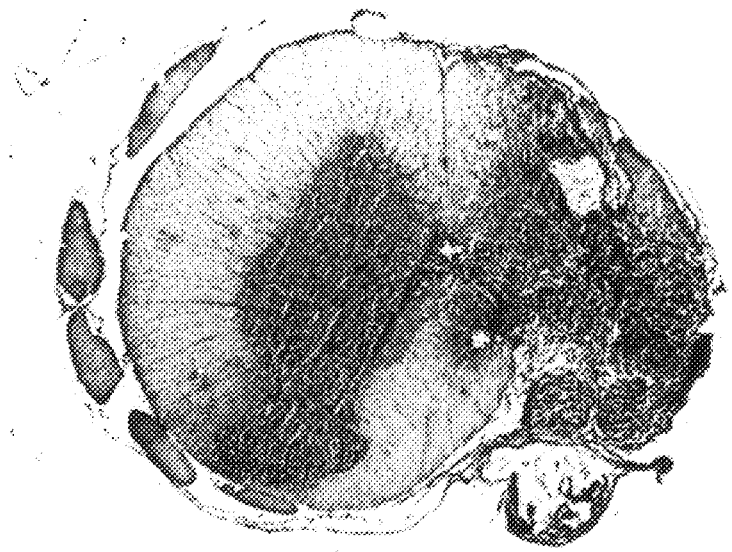
FIG. 6 is a photomicrograph of a section of a hemisected spinal cord 60 days after injury, treated with an inert gel.
Figure 7:
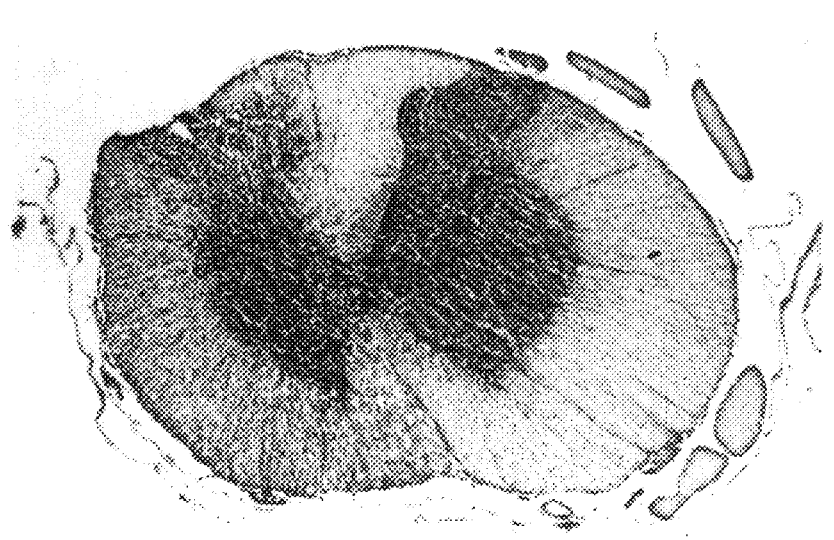
FIG. 7 is a photomicrograph of a section of a hemisected spinal cord 60 days after injury, treated with N-CAM, without a tube or other prosthesis.

The results of morphological studies are illustrated in FIGS. 6 and 7. FIG. 6 is a micrograph of a section of a hemisected spinal cord 60 days after injury and treatment with an inert gel. FIG. 7 is a micrograph of a section of a hemisected spinal cord 60 days after injury and treatment with N-CAM, without any tube or other prosthesis around the site of injury. The contrast between FIGS. 6 and 7 is apparent even to the layperson.

It should be noted that the spinal cord injury tested here—complete hemisection of the spinal cord—is a more severe injury than is typically suffered by human spinal cord patients. Most spinal cord injuries in humans do not result in complete severing of axons (fibers), but instead have sufficient strain, twisting, or laceration of the neurons to cause loss of function.

Experiments in rats involving severe laceration of the full width of the spinal cord, but otherwise substantially as described above for the hemisection experiments, will be performed soon. It is expected that the rats with lacerated spinal cords, treated with N-CAM, will show recovery comparable to that of the rats with hemisected spinal cords.

The technique will next be tested in monkeys with completely transected motor nerves, followed by testing in monkeys with completely transected spinal cords. Because rat neurons are similar to primate neurons in many ways, it is expected that the monkeys will show recoveries comparable to those reported above for rats.

Once appropriate regulatory requirements have been met, the technique will be tested in human accident victims having motor nerve injuries, and in human accident victims having spinal cord injuries. Because rat neurons are similar to human neurons in many ways, it is expected that the human patients will show recoveries comparable to those reported above for rats.

The techniques of this invention will be used in cases of recent trauma to a nerve or a spinal cord, and also in cases of older injuries. Initially, treatments otherwise as described above will be conducted on recent injuries; if the results are successful (as is expected), treatments will next be tried on three-day-old injuries; if those results are successful, treatments will then also be tried on progressively older injuries.

It should be noted that the structure of N-CAM is highly conserved between species; considerable structural overlap occurs in N-CAM from fruit flies, amphibians, birds, horses, non-human primates, and humans. See S. Hoffman et al., "Evolutionary Conservation of Key Structures and Binding Functions of N-CAM," *Proc. Natl. Acad. Sci. (USA)*, vol. 81, pp. 6881–6884 (1984). Thus non-species-specific use of N-CAM is possible.

While the 180 kD large domain of N-CAM may also be of use in the present invention, it is believed (without wishing to be bound by this theory) that the 140 kD domain is most active, and can be used alone in the practice of the present invention. This 140 kD domain has been reported to be the strongest of the three domains in promoting neural fiber outgrowth in embryonic brains. The 140 kD domain is encoded by 6.2 kb of the N-CAM gene: namely, exons 1–14, 16, 17, and 19. See B. A. Cunningham et al., "Neural Cell Adhesion Molecule: Structure, Immunoglobulin-like Domains, Cell Surface Modulation, and Alternative RNA Splicing," *Science*, vol. 236, pp. 799–806 (1987); J. J. Hemperly et al., "Sequence of a cDNA Clone Encoding the Polysialic Acid-Rich and Cytoplasmic Domains of the Neural Cell Adhesion Molecule N-CAM," *Proc. Natl. Acad. Sci.(USA)*, vol. 83, pp. 3037–3040 (1986); and P. Doherty et al., "Alternative Splicing of the Cytoplasmic Domain of the Neural Cell Adhesion Molecule Alters its Ability to Act as a Substrate for Neurite Outgrowth," *J. Neurochem.*, vol. 58, pp. 2338–2341 (1992).

The combined immunoglobulin-like domains, domains I-V of the 140 kD domain (52 kD; base pairs 223–1622) are believed to have particular promise in the practice of this invention. The combined immunoglobulin-like domains have been reported to be strong promoters of neural fiber outgrowth in embryos. See T. Frei et al., "Different Extracellular Domains of the Neural Cell Adhesion Molecule (N-CAM) Are Involved in Different Functions," *J. Cell Biol.*, vol. 118, pp. 177–194 (1992); and B. A. Cunningham et al., "Neural Cell Adhesion Molecule: Structure, Immunoglobulin-like Domains, Cell Surface Modulation, and Alternative RNA Splicing," Science, vol. 236, pp. 799–806 (1987).

Of all these regions, the immunoglobulin-like domain I (13 kD; base pairs 223–487) may be the domain with the single largest effect in practicing the present invention. That domain may be the strongest promoter of neurite outgrowth in embryonic development.

It is intended that the scope of the present invention includes the use of N-CAM as recited, or of any portion of N-CAM that is active in promoting the regrowth of neurons or axons. As used in the claims, an "active" portion of N-CAM is a domain or subdomain of N-CAM that promotes the regrowth of injured neurons or axons. It has not previously been suggested that a portion of N-CAM may be used to promote the regrowth of injured neurons, either with or without a tube.

To obtain N-CAM or its subunits one can, for example, use the protein or peptide(s) expressed by a cloned N-CAM gene or portion of that gene. See J. Hemperly et al., "Sequence of a cDNA Clone Encoding the Polysialic Acid-Rich and Cytoplasmic Domains of the Neural Cell Adhesion Molecule," *Proc. Natl. Acad. Sci. (USA)*, vol. 83, pp. 3037–3040 (1986); C. Goridis et al., "Isolation of Mouse N-CAM cDNA: Detection and Cloning Using Monoclonal Antibodies," *Eur. Mol. Biol. Organ.*, vol. 4, pp. 631–635 (1985); and T. Frei et al., "Different Extracellular Domains of the Neural Cell Adhesion Molecule (N-CAM) Are Involved in Different Functions," *J. Cell Biol.*, vol. 118, pp. 177–194 (1992); the complete disclosures of each of which are incorporated by reference. To mimic the effects of post-translational modification of the expressed protein or peptide, it is believed that simple physical mixing of the expressed protein or peptide with polysialic acid (about 1% to about 20% by weight, preferably about 4% by weight) will suffice. Without wishing to be bound by this theory, it is believed that the primary role of the polysialic acid is to alter the cellular membrane in such a way that the N-CAM protein is taken up by the cell, and that the polysialic acid will perform this role if merely mixed with the expressed N-CAM protein or a subunit of that protein.

N-CAM or an active portion of N-CAM may be administered to the site of neural injury in a pharmaceutically acceptable carrier. The primary function of the carrier is to retain the N-CAM or active portion of N-CAM at the site of the injury for a time long enough to initiate the regeneration process; this time will typically be approximately seven days. It is preferred that the carrier should be absorbed, biodegraded, or otherwise removed naturally by the host after a time sufficient to initiate the regeneration process. The carrier should not, of course, tend to support an adverse reaction such as inflammation at the site of neural injury. Examples of acceptable carriers include agarose, glycerol, and phosphate-buffered saline.

While these methods for repairing neurons are expected to work with most, if not all, vertebrate species, for practical reasons it is expected that most applications of this invention will be in mammals, especially in humans, and perhaps also in horses and other companion animals.

The entire disclosures of all references cited in this specification are hereby incorporated by reference.

Sequences for the human N-CAM gene and amino acid sequence are listed below as SEQ ID NO. 1 and SEQ ID NO. 2, respectively.

I claim:

1. A process for repairing one or more injured mammalian neurons, wherein the site of neural injury is within the spinal cord, comprising applying to the site of neural injury an agent comprising a compound selected from the group consisting of:
   (a) exogenous neural cell adhesion molecule;
   (b) the 170–200 kD domain of the neural cell adhesion molecule;
   (c) the 140 kD domain of the neural cell adhesion molecule;
   (d) the immunoglobulin-like domains I–V of the 140 kD domain of the neural cell adhesion molecule, said immunoglobulin-like domains I–V having a molecular weight of 52 kD; and
   (e) the immunoglobulin-like domain I of the 140 kD domain of the neural cell adhesion molecule, said immunoglobulin-like domain I having a molecular weight of 13 kD.

2. A process as recited in claim 1, wherein said process is performed for a plurality of injured neurons, wherein each of the injured neurons has a site of injury within the spinal cord.

3. A process as recited in claim 2, wherein the injured neurons are human neurons.

4. A process as recited in claim 1, wherein said agent additionally comprises polysialic acid.

5. A process as recited in claim 1, wherein said agent comprises the neural cell adhesion molecule.

6. A process as recited in claim 1, wherein said agent comprises the 170–200 kD domain of the neural cell adhesion molecule.

7. A process as recited in claim 1, wherein said agent comprises the 140 kD domain of the neural cell adhesion molecule.

8. A process as recited in claim 1, wherein said agent comprises the immunoglobulin-like domains I–V of the 140 kD domain of the neural cell adhesion molecule, said immunoglobulin-like domains I–V having a molecular weight of 52 kD.

9. A process as recited in claim 1, wherein said agent comprises the immunoglobulin-like domain I of the 140 kD domain of the neural cell adhesion molecule, said immunoglobulin-like domain I having a molecular weight of 13 kD.

10. A process for repairing one or more injured mammalian neurons, wherein the site of neural injury is within the spinal cord, said process comprising applying to the site of neural injury an agent in the absence of any prosthetic device or tube surrounding the immediate site of the neural injury, wherein said agent comprises a compound selected from the group consisting of:
   (a) exogenous neural cell adhesion molecule;
   (b) the 170–200 kD domain of the neural cell adhesion molecule;
   (c) the 140 kD domain of the neural cell adhesion molecule;
   (d) the immunoglobulin-like domains I–V of the 140 kD domain of the neural cell adhesion molecule, said immunoglobulin-like domains I–V having a molecular weight of 52 kD; and
   (e) the immunoglobulin-like domain I of the 140 kD domain of the neural cell adhesion molecule, said immunoglobulin-like domain I having a molecular weight of 13 kD.

11. A process as recited in claim 10, wherein said process is performed for a plurality of injured neurons, wherein each of the injured neurons has a site of injury within the spinal cord.

12. A process as recited in claim 11, wherein the injured neurons are human neurons.

13. A process as recited in claim 10, wherein said agent additionally comprises polysialic acid.

14. A process as recited in claim 10, wherein said agent comprises the neural cell adhesion molecule.

15. A process as recited in claim 10, wherein said agent comprises the 170–200 kD domain of the neural cell adhesion molecule.

16. A process as recited in claim 10, wherein said agent comprises the 140 kD domain of the neural cell adhesion molecule.

17. A process as recited in claim 10, wherein said agent comprises the immunoglobulin-like domains I–V of the 140 kD domain of the neural cell adhesion molecule, said immunoglobulin-like domains I–V having a molecular weight of 52 kD.

18. A process as recited in claim 10, wherein said agent comprises the immunoglobulin-like domain I of the 140 kD domain of the neural cell adhesion molecule, said immunoglobulin-like domain I having a molecular weight of 13 kD.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1644 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x ) PUBLICATION INFORMATION:
        ( A ) AUTHORS: Dickson, G.
            Gower, H. J.
            Barton, C. H.
            Prentice, H. M.
            Elsom, V. L.
            Moore, S. E.
            Cox, R. D.
            Quinn, C.
            Putt, W.
            Walsh, F. S.
        ( B ) TITLE: Human Muscle Neural Cell Adhesion Molecule
        ( N - C A M ): Identification of a Muscle-Specific
            Sequence in the Extracellular Domain
        ( C ) JOURNAL: Cell
        ( D ) VOLUME: 50
        ( F ) PAGES: 1119-1130
        ( G ) DATE: 1987

( x i ) SEQUENCE DESCRIPTION: SEQ ID NO:1:

```
GAATTCATCC  TTGTTCAAGC  AGACACCCCC  TCTTCACCAT  CCATCGACCA  GGTGGAGCCA      60

TACTCCAGCA  CAGCCCAGGT  GCAGTTTGAT  GAACCAGAGG  CCACAGGTGG  GGTGCCCATC     120
```

```
CTCAAATACA  AAGCTGAGTG  GAGAGCAGTT  GGTGAAGAAG  TATGGCATTC  CAAGTGGTAT        180

GATGCCAAGG  AAGCCAGCAT  GGAGGGCATC  GTCACCATCG  TGGGCCTGAA  GCCCGAAACA        240

ACGTACGCCG  TAAGGCTGGC  GGCGCTCAAT  GGCAAAGGGC  TGGGTGAGAT  CAGCGCGGCC        300

TCCGAGTTCA  AGACGCAGCC  AGTCCGGGAA  CCCAGTGCAC  CTAAGCTCGA  AGGGCAGATG        360

GGAGAGGATG  GAAACTCTAT  TAAAGTGAAC  CTGATCAAGC  AGGATGACGG  CGGCTCCCCC        420

ATCAGACACT  ATCTGGTCAG  GTACCGAGCG  CTCTCCTCCG  AGTGGAAACC  AGAGATCAGG        480

CTCCCGTCTG  GCAGTGACCA  CGTCATGCTG  AAGTCCCTGG  ACTGGAATGC  TGAGTATGAG        540

GTCTACGTGG  TGGCTGAGAA  CCAGCAAGGA  AAATCCAAGG  CGGCTCATTT  TGTGTTCAGG        600

ACCTCGGCCC  AGCCCACAGC  CATCCCAGCC  AACGGCAGCC  CCACCTCAGG  CCTGAGCACC        660

GGGGCCATCG  TGGGCATCCT  CATCTTCGTC  CTGCTCCTGG  TGGTTGTGGA  CATCACCTGC        720

TACTTCCTGA  CAAGTGTGG   CCTGTTCATG  TGCATTGCGG  TCAACCTGTG  TGGAAAAGCC        780

GGGCCCGGGG  CCAAGGGCAA  GGACATGGAG  GAGGGCAAGG  CCGCCTTCTC  GAAAGATGAG        840

TCCAAGGAGC  CCATCGTGGA  GGTTCAACG   GAGGAGGAGA  GGACCCAAA   CCATGATGGA        900

GGGAAACACA  CAGAGCCCAA  CGAGACCACG  CCACTGACGG  AGCCCGAGAA  GGCGCCCGTA        960

GAAGCAAAGC  CAGAGTGCCA  GGAGACAGAA  ACGAAGCCAG  CGCCAGCCGA  AGTCAAGACG       1020

GTCCCCAATG  ACGCCACACA  GACAAAGGAG  AACGAGAGCA  AAGCATGATG  GGTGAAGAGA       1080

ACCGAGCAAA  GATCAAAATA  AAAAGTGACA  CAGCAGCTTC  ACCAGAGCAT  TCCAACACC        1140

ACAGACACAC  ACACGCACGC  ACACACACAA  ACACACATGC  ACACACACAC  ATCTCATTTC       1200

TCTAGTGTCT  TTTGCCTTTA  AAAAAAACTA  AACAGATAAA  ACATGGGAAT  CTCCTTTTTG       1260

TAGGTTTATA  GAAAGGGTCC  CTTTGTTGCA  CACTCACTTG  TAAGAAAATG  AGACAAAAAG       1320

GTTAAACCCA  CAGCCAAACT  AGGACACTCC  GTTCCCTGAA  ACCGTTAAAA  AATCAAACAA       1380

AAGGACCCCA  AATTAAGAAT  CTAGGAAGCT  CAGAAACGAA  ATCTAGGTTC  AGGAAGACCA       1440

CACTTGGTGT  TACCCGATTG  GCACAGACCA  GTTCAGAGA   AATACTTTCA  GGCACTAAGA       1500

CTAATCGAAT  GAACAAAGTC  CACAGTTTAT  TTTTATACTT  TCAGTCAAGT  TTGAACTCTG       1560

TAAAACCTCA  TAAATAAGTT  ATAATTTCTG  TTCACTTTGT  ATTTGTTCAG  TATGCAAAGT       1620

GTGTCACCCT  TTCTAGCTGA  ATTC                                                 1644
```

( 2 ) INFORMATION FOR SEQ ID NO:2:

( i ) SEQUENCE CHARACTERISTICS:
        ( A ) LENGTH: 355 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:2:

```
Glu  Phe  Ile  Leu  Val  Gln  Ala  Asp  Thr  Pro  Ser  Ser  Pro  Ser  Ile  Asp
 1              5                        10                       15

Gln  Val  Glu  Pro  Tyr  Ser  Ser  Thr  Ala  Gln  Val  Gln  Phe  Asp  Glu  Pro
                20                       25                       30

Glu  Ala  Thr  Gly  Gly  Val  Pro  Ile  Leu  Lys  Tyr  Lys  Ala  Glu  Trp  Arg
```

-continued

|  | 35 |  |  |  | 40 |  |  |  | 45 |  |  |  |  |  |
|---|---|---|---|---|---|---|---|---|---|---|---|---|---|---|
| Ala | Val 50 | Gly | Glu | Glu | Val | Trp 55 | His | Ser | Lys | Trp | Tyr 60 | Asp | Ala | Lys | Glu |
| Ala 65 | Ser | Met | Glu | Gly | Ile 70 | Val | Thr | Ile | Val | Gly 75 | Leu | Lys | Pro | Glu | Thr 80 |
| Thr | Tyr | Ala | Val | Arg 85 | Leu | Ala | Ala | Leu | Asn 90 | Gly | Lys | Gly | Leu | Gly 95 | Glu |
| Ile | Ser | Ala | Ala 100 | Ser | Glu | Phe | Lys | Thr 105 | Gln | Pro | Val | Arg | Glu 110 | Pro | Ser |
| Ala | Pro | Lys 115 | Leu | Glu | Gly | Gln | Met 120 | Gly | Glu | Asp | Gly | Asn 125 | Ser | Ile | Lys |
| Val | Asn 130 | Leu | Ile | Lys | Gln | Asp 135 | Asp | Gly | Gly | Ser | Pro 140 | Ile | Arg | His | Tyr |
| Leu 145 | Val | Arg | Tyr | Arg | Ala 150 | Leu | Ser | Ser | Glu | Trp 155 | Lys | Pro | Glu | Ile | Arg 160 |
| Leu | Pro | Ser | Gly | Ser 165 | Asp | His | Val | Met | Leu 170 | Lys | Ser | Leu | Asp | Trp 175 | Asn |
| Ala | Glu | Tyr | Glu 180 | Val | Tyr | Val | Val | Ala 185 | Glu | Asn | Gln | Gln | Gly 190 | Lys | Ser |
| Lys | Ala | Ala 195 | His | Phe | Val | Phe | Arg 200 | Thr | Ser | Ala | Gln | Pro 205 | Thr | Ala | Ile |
| Pro | Ala 210 | Asn | Gly | Ser | Pro | Thr 215 | Ser | Gly | Leu | Ser | Thr 220 | Gly | Ala | Ile | Val |
| Gly 225 | Ile | Leu | Ile | Phe | Val 230 | Leu | Leu | Leu | Val | Val 235 | Val | Asp | Ile | Thr | Cys 240 |
| Tyr | Phe | Leu | Asn | Lys 245 | Cys | Gly | Leu | Phe | Met 250 | Cys | Ile | Ala | Val | Asn 255 | Leu |
| Cys | Gly | Lys | Ala 260 | Gly | Pro | Gly | Ala | Lys 265 | Gly | Lys | Asp | Met | Glu 270 | Glu | Gly |
| Lys | Ala | Ala 275 | Phe | Ser | Lys | Asp | Glu 280 | Ser | Lys | Glu | Pro | Ile 285 | Val | Glu | Val |
| Arg | Thr 290 | Glu | Glu | Glu | Arg | Thr 295 | Pro | Asn | His | Asp | Gly 300 | Gly | Lys | His | Thr |
| Glu 305 | Pro | Asn | Glu | Thr | Thr 310 | Pro | Leu | Thr | Glu | Pro 315 | Glu | Lys | Ala | Pro | Val 320 |
| Glu | Ala | Lys | Pro | Glu 325 | Cys | Gln | Glu | Thr | Glu 330 | Thr | Lys | Pro | Ala | Pro 335 | Ala |
| Glu | Val | Lys | Thr 340 | Val | Pro | Asn | Asp | Ala 345 | Thr | Gln | Thr | Lys | Glu 350 | Asn | Glu |
| Ser | Lys | Ala 355 |  |  |  |  |  |  |  |  |  |  |  |  |  |